United States Patent [19]

Bick et al.

[11] 4,027,013

[45] May 31, 1977

[54] CLOTTABLE FIBRINOGEN FREE FACTOR VIII AND ALBUMIN PRODUCT AND PROCESS

[75] Inventors: Rodger L. Bick, Los Angeles; Lajos F. Fekete, Costa Mesa, both of Calif.

[73] Assignees: William L. Wilson; Rodger L. Bick; Lajos F. Fekete, all of Santa Monica, Calif.

[22] Filed: Jan. 22, 1976

[21] Appl. No.: 651,614

[52] U.S. Cl. .............................. 424/101; 260/112 B
[51] Int. Cl.² .................... A61K 35/14; C07G 7/00
[58] Field of Search ................. 424/101; 260/112 B

[56] References Cited

OTHER PUBLICATIONS

Kevy, Chem. Abst., vol. 78 (1973), p. 69608g.

*Primary Examiner*—Sam Rosen

[57] ABSTRACT

Lyophilizable, clottable fibrinogen free, Factor VIII is produced on a commercial scale from a fibrinogen containing Factor VIII concentrate by sequentially, precipitating a major portion of the clottable fibrinogen by the addition of an ethylene oxide-polyoxypropylene block copolymer, clotting the remainder of the clottable fibrinogen by the addition of a small amount of a thrombin mimetic enzyme which does not decrease the potency of the Factor VIII, and adding human albumin to the resultant clottable fibrinogen free Factor VIII to stabilize its potency during lyophilization.

13 Claims, No Drawings

CLOTTABLE FIBRINOGEN FREE FACTOR VIII AND ALBUMIN PRODUCT AND PROCESS

This invention relates to the preparation of a Factor VIII product which is free of clottable fibrinogen. Factor VIII is one of the trace proteins which is required in the clotting of human blood. When Factor VIII is missing from a patient's blood or is for some reason biologically inactive, normal clotting does not take place. One treatment for such a patient is to add normal Factor VIII to the patient's blood by injection. A problem arises in this regard because previously it was not feasible on a commerical scale to separate Factor VIII and fibrinogen. Thus, previously a highly potent commercially available Factor VIII concentrate would also inevitably contain a significant concentration of fibrinogen. The injection of an excessive amount of fibrinogen often resulted in kidney failure. For this reason it was often impossible to administer an effective dosage of Factor VIII to a patient who needed this material for normal clotting.

According to the present invention, a Factor VIII concentrate is prepared which is free of clottable fibrinogen. The procedures are suitable for the production of high yields of Factor VIII concentrate on a commercial scale. The product is suitable for injection into hemophiliac patients. Also, this clottable fibrinogen free Factor VIII concentrate may, if desired, be lyophilized for purposes of storage and transportation.

In general the present invention includes a procedure whereby a substantial proportion of the clottable fibrinogen (more than approximately 90 percent) is precipitated in an initial separation step with the Factor VIII remaining in solution. The precipitated fibrinogen is separated and discarded. The resulting fibrinogen lean supernate is concentrated by precipitation and reconstitution to reduce the volume of liquid. The reconstituted Factor VIII-fibrinogen precipitate is treated with a small amount of a thrombin mimetic enzyme which causes the remaining clottable fibrinogen to clot but does not significantly impair the biological activity of the Factor VIII. These thrombin mimetic enzymes occur naturally in various snake venoms and are isolated and purified for use in the present invention. The Factor VIII remains in the supernate and the clotted fibrinogen is discarded. The Factor VIII which is now free of clottable fibrinogen is again precipitated and the supernate is discarded. The resulting Factor VIII precipitate is redissolved in a small amount of saline solution, and human albumin is added to stabilize the Factor VIII during lyophilization. The yield of Factor VIII is as high as approximately 90 percent, and the lyophilized product upon reconstitution exhibits substantially all of the Factor VIII bilolgical activity that it possessed prior to lyophilizaton.

The entire procedure except for lyophilization may be conducted at room temperature and preferably at temperatures ranging from about 15° to 30° centigrade, although temperatures as low as 10° centigrade and as high as 35° centigrade may be used. Temperatures below about 10° centigrade tend to impair the potency of the Factor VIII, and temperatures in excess of about 35 degress centigrade impair the biological activity of the Factor VIII. At a temperature of about 40° centigrade the potency of the Factor VIII is completely destroyed.

In general, the salt concentration of the Factor VIII solutions which contain the Factor VIII are adjusted to physiological values (0.15 molar sodium chloride), although salt concentrations somewhat above and below physiological values may be used if desired. After the Factor VIII has been separated from the fibrinogen, it is somewhat sensitive to salt concentrations so that salt concentrations of about 0.05 to 0.25 molar sodium chloride are preferred for use with Factor VIII containing solutions after the fibrinogen has been removed. Prior to the removal of fibrinogen, salt concentrations of from about 0.05 to 0.50 molar sodium chloride may be employed if desired without impairing the potency of the Factor VIII or the thrombin mimetic enzyme, and without precipitating the Factor VIII from the liquid phase. Sodium citrate may be utilized throughout the precedure and in the final lyophilized product if desired in addition to sodium chloride.

In general the pH of the solutions utilized in the preparation of the clottable fibrinogen Factor VIII product may range from about 6.0 to 8.0 and preferably from about 6.5 to 7.0. Below a pH of 6 the fibrinogen forms clots which carry the Factor VIII with them, and above a pH of about 8 the yields are so low that substantially no Factor VIII is recovered. After the fibrinogen has been separated from the Factor VIII, it becomes somewhat more sensitive to pH, and pH values should be maintained in the range of from about 6.7 to 7.0.

The initial precipitation of a substantial portion of the fibrinongen as well as the subsequent precipitations of Factor VIII containing materials is conveniently accomplished by utilizing different concentrations of certain block copolymers. The particular block copolymers that are utilized in these selective precipitation procedures are conveniently prepared by condensing ethylene oxide with polyoxypropylene polymer. The resultant condensation products are well known materials which can be represented by the following structural formula:

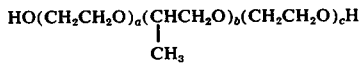

Block copolymers which are suitable for these purposes are available from Wyandotte Chemicals Corp. under the designations "Pluronic F-38" and "Pluronic F-68." The Pluronic F-38 material contains about 80 percent polyoxyethylene units and the polyoxypropylene polymer portion of the molecule has a molecular weight of about 950. The condensation product has a molecular weight of about 4,750. The Pluronic F-68 material also contains about 80 percent polyoxyethylene units and the polyoxypropylene polymer portion of the molecule has a molecular weight of about 1,750 with the total molecular weight of the condensation product being about 8,750. In general these block copolymers contain at least about 50 percent ethylene oxide in the molecule, and the polyoxypropylene polymer portion of the molecule has a molecular weight of at least about 900. The block copolymers must be water soluble at concentrations of at least about 20 percent on a weight per volume basis at temperatures of from about 10° to 35° centigrade. These materials must be nontoxic.

In general the initial separation step in which a substantial portion of the fibrinogen is separated by precipitation from a Factor VIII containing supernate is accomplished at a concentration of from about 1 to 4.5 gram percent (grams per 100 cubic centimeters), and preferably 3 to 4 gram percent of the block copolymer at a salt concentration of about 0.15 molar sodium chloride and a temperature of from about 15° to 30° centigrade. At concentrations below about 1 gram percent the procedure does not remove a sufficient amount of fibrinogen, and at concentrations above about 4.5 gram percent a substantial portion of the Factor VIII is also precipitated. The partial separation of fibrinogen and Factor VIII using Pluronic F-38 and F-68 is suggested in Fekete et al U.S. Pat. No. 3,770,631.

In subsequent steps where it is desired to precipitate all of the Factor VIII the concentration of the block copolymer ranges from about 6 to 10 gram percent, and preferably from about 8 to 10 gram percent. Below 6 gram percent block copolymer the yield of Factor VIII is very low. Above about 10 gram percent substantially all of the bacteria which may be present are precipitated. As the temperataure is decreased below about 15 degrees centigrade the concentration of the block copolymer should be reduced slightly so as to avoid the precipitation of excessive amounts of bacteria which may be present in blood plasma fractions.

The thrombin mimetic enzymes or regents are used to clot and thus separate the residual fibrinogen which remains after the initial fibrinogen separation step. These reagents, unlike thrombin, do not impair the biological activity of Factor VIII. These thrombin mimetic reagents are extracted from the venom of various snakes including, for example, the Malayan pit-viper (Agkistrodon rhodostoma), the South American snake (Bothrops atrox), and the snakes (Crotalus terrificus) and (Crotalus adamanteus). These thrombin mimetic enzymes are available under the brand names "Arvin" (Twyford Laboratories, London, England), "Ancord" (Abbott Laboratories, North Chicago, Illinois), and "Reptillase" (Abbott Laboratories, North Chicago, Illinois). It had previously been suggested that these thrombin mimetic enzymes might be used to prepare low yields of Factor VIII which is free of fibrinogen, Greed D.: "A Simple Method for the Purification of Factor VIII (Antihemophiliac Factor) Employing Snake Venom." J. Lab. Clin. Med. 77: 153–158 (1971).

The respective fibrinogen and Factor VIII precipitation steps, other than the clotting step, may be carried out using precipitation reagents other than the ethylene oxide-polyoxypropylene block copolymer condensation products; for example, polyethylene glycol may be used with substantially diminished yields of Factor VIII, as taught, for example, by A. Polson and C. Ruiz-Bravo: "Fractionation of Plasma with Polyethylene Glycol" Vox Sang. 23: 107–118 (1972). Ethanol, ammonium sulfate, and glycine require the use of low temperatures which are destructive to the potency of highly concentrated Factor VIII. Dialysis procedures may also be used if desired, although they are not generally economically feasible. The block copolymers produce the best results and are preferred. Polyethylene glycol produces acceptable results for a commercial scale operation.

The potency of the thrombin mimetic enzymes is given herein in terms of thrombin units with one Iowa unit of thrombin being equal to one unit of thrombin mimetic enzyme. One Iowa unit of thrombin is that amount of thrombin which will clot standard fibrinogen in 15 seconds at 28° centigrade. The biological activity or potency of Factor VIII is measured in units of Factor VIII with one unit of Factor VIII being that amount of Factor VIII which occurs in one milliliter of freshly drawn pooled plasma. The Factor VIII is measured in units as is the thrombin mimetic enzyme, because this protein is present in such minute quantities that its weight and volume cannot be detected with conventional laboratory equipment.

The concentration of thrombin mimetic enzyme which is utilized in the preparation of clottable fibrinogen free Factor VIII should be kept as low as possible. In high concentrations, the enzyme attacks the Factor VIII and also tends to be carried over into the final product. The enzyme if injected into a patient will cause excessive bleeding, even though it causes the clotting of fibrinogen in vitro. Thus, the injection of the enzyme into a hemophiliac patient is very undesirable. By removing a substantial portion of the fibrinogen before the thrombin mimetic enzyme is used and concentrating the resultant fibrinogen lean material, it is possible to utilize enzyme concentrations which do not significantly impair the potency of the Factor VIII. The action of the enzyme appears to be catalytic in nature so that it is effective even in very minute concentrations. The concentrations should, however, be adequate to cause the clotting of all of the clottable fibrinogen in the admixture within approximately 24 hours. Lower concentrations of the enzyme will result in complete clotting of the fibrinogen but several days will be requied to accomplish this. The Factor VIII tends to lose its biological activity if it remains in solution for too long a period of time. For this reason extremely low concentrations of thrombin mimetic enzyme do not produce satisfactory yields of Factor VIII. Also, extended clotting times permit the growth of undesired bacteria in the admixture. Concentrations of thrombin mimetic enzyme which are effective in clotting the fibrinogen within approximately 24 hours at approximately 22° centigrade without significantly impairing the potency of the Factor VIII are from about 0.5 units of enzyme to 3 units of enzyme per 1,000 milligrams of fibrinogen, and preferably from about 0.75 units of enzyme to 2 units of enzyme per 1,000 milligrams of fibrinogen. At a concentration of 0.15 units of enzyme to 1,000 milligrams of fibrinogen clotting requires approximately 40 hours, and at a concentration of 3 units of enzyme per 1,000 milligrams of fibrinogen the yield of Factor VIII drops to approximately 50 percent.

In general, the concentration of clottable fibrinogen should be reduced to less than approximately 0.2 milligrams of clottable fibrinogen per unit of Factor VIII before the thrombin mimetic enzyme is used to clot the remaining clotting fibrinogen. At higher concentrations of fibrinogen excessive amounts of thrombin mimetic enzyme relative to the Factor VIII are required to accomplish clotting within the desired time and the potency of the Factor VIII is impaired. Preferably the clottable fibrinogen lean Factor VIII concentrate contains less than about 0.15 milligrams of fibrinogen per unit of Factor VIII. Fresh pooled plasma contains about 2 milligrams of fibrinogen per unit of Factor VIII.

After the initial fibrinogen removal step, the clottable fibrinogen lean Factor VIII aqueous admixture is concentrated to a Factor VIII potency of at least approximately 15 and preferably at least about 35 units per milliliter so as to avoid excessive dilution of the thrombin mimetic enzyme.

Factor VIII tends to lose its potency if it is stored and transported in the liquid form. Accordingly, it is necessary to lyophilize the Factor VIII for purposes of transportation and storage. Prior to the present invention it had generally been believed that it was not possible to lyophilize clottable fibrinogen free Factor VIII without substantially destroying its potency. According to the present invention, the addition of human albumin to the clottable fibrinogen free Factor VIII material will stabilize the Factor VIII so that it may be lyophilized and reconstituted without losing any significant amount of its potency. At least about 0.5 gram percent of human albumin (grams per 100 milliliters) is required to stabilize the Factor VIII during lyophilization. Preferably, the concentration of human albumin in the clottable fibrinogen free Factor VIII concentrate solution is at least one gram percent. Greater quantities of human albumin may be used up to the limits of the solubility of this material; however, no advantages are gained by increasing the quantity of human albumin, and the increased quantities tend to render the product less suitable for injection into hemophiliac patients. The lyophilized product generally contains at least about 10 and preferably at least about 20 units of Factor VIII per milligram of human albumin.

The following examples are submitted to illustrate and not to limit the invention.

EXAMPLE I

The purpose of this example is to illustrate the preparation of high potency fibrinogen free Factor VIII concentrate by a procedure which is suited for use on a commercial scale.

A crude fibrinogen containing liquid Factor VIII concentrate was selected as the starting material. This Factor VIII concentrate had a potency of 4.7 units per milliliter of Factor VIII, as determined by in vitro bioassay procedures. The 266 milliliter starting sample of this Factor VIII concentrate contained 2,700 milligrams of fibrinogen per 100 milliliters of sample. The total weight of fibrinogen in the 266 milliliter starting sample was 7,182 milligrams, as determined by conventional in vitro bioassay procedures.

INITIAL FIBRINOGEN PRECIPITATION

The pH of this 266 milliliter sample was adjusted to a value of 6.5, and the temperature was maintained at about 22 degrees centigrade.

About 3.5 percent on a weight per volume basis (grams per 100 cubic centimeters) of a block copolymer was added to the sample of crude Factor VIII concentrate. The block copolymer was an ethylene oxide-propylene glycol condensation product in which about 80 percent of the block copolymer consisted of polyoxyethylene units. The polyoxypropylene portion of the polymer had a molecular weight of about 1,750. The total molecular weight of the copolymer was about 8,750. This material is available commercially from Wyandotte Chemicals Corp. under the designation "Pluronic F-68." The resulting admixture containing the dissolved block copolymer was stirred for about 20 minutes during which period of time a precipitate formed. The precipitate was centrifuged down at 5,000 gravities for a period of about 15 minutes. The Factor VIII containing supernate was recovered, and the precipitate was discarded. The precipitate consisted primarily of fibrinogen. Samples of the resulting fibrinogen lean retained supernate were withdrawn and analyzed by in vitro bioassay procedures for Factor VIII potency and fibrinogen concentration. The Factor VIII potency was found to be about 4.8 units per milliliter. The supernate contained about 200 milligrams of fibrinogen. The volume of the supernate remaining after the samples had been withdrawn for assay purposes was 234 milliliters.

INITIAL FACTOR VIII PRECIPITATION

The pH of this 234 milliliter sample was adjusted to a value of about 6.88. The temperature of this sample was about 22° centigrade. An amount of the same block copolymer utilized previously (Pluronic F-68) sufficient to bring the total concentration of block copolymer to 10 percent on a weight per volume basis (grams per 100 cubic centimeters) was added to the mixture. The admixture was stirred for about 15 minutes during which period of time a precipitate formed therein. The Factor VIII containing precipitate was centrifuged down for about 15 minutes at 5,000 gravities. Substantially all of the Factor VIII and fibrinogen were in this precipitate. The supernate was discarded. The salt concentration of the crude fibrinogen containing Factor VIII sample which was used as the starting material in this example was at the physiological value of 0.15 molar sodium chloride. This salt concentration remained at about this value in the liquid phase throughout the procedure to this point. The precipitate recovered from this step was very rich in Factor VIII.

REDISSOLVED REDUCED FACTOR VIII

This Factor VIII rich precipitate was redissolved in citrated saline (1 part by volume of 0.1 molar sodium citrate and 4 parts by volume of 0.15 molar sodium chloride solution). The volume of the redissolved reduced Factor VIII rich precipitate was 30 milliliters. The pH was adjusted to a value of 6.88 and the temperature was maintained at a value of about 22° centigrade. The Factor VIII potency, as determined by conventional in vitro bioassay procedures, was about 50 units per milliliter. The 30 milliliters of redissolved reduced precipitate contained about 200 milligrams of fibrinogen.

ENZYMATIC SEPARATION OF FIBRINOGEN

The remaining fibrinogen was separated from the redissolved reduced precipitate by adding 0.2 units of a thrombin mimetic enzyme to the redissolved reduced precipitate. The concentration of enzyme was about 1 unit of enzyme to 1,000 milligrams of fibrinogen. The thrombin mimetic enzyme was a purified enzyme fraction of Malayan pit-viper venom which is available under the brand name "Ancrod" from Abbott Laboratories. This enzyme does not activate Factor VIII so that the Factor VIII retained its potency. A solid mass (clot) formed in the resultant admixture in about 24 hours. The resultant mass was centrifuged at 5,000 gravities for about 20 minutes, and the Factor VIII rich supernate was recovered. All of the clottable fibrinogen was removed in the solid mass. Some potency of Factor VIII was lost in this step, but the loss was less than approximately 10 percent and was not considered to be significant.

FIBRINOGEN FREE FACTOR VIII PRECIPITATE

The pH of the Factor VIII rich fibrinogen free concentrate was checked to insure that it remained at a value of 6.88. The above described block copolymer (Pluronic F-68) was added to the fibrinogen free supernate. The quantity of block copolymer was sufficient to bring the concentration of block copolymer in the supernate to a value of 10 percent on a weight per volume basis (grams per 100 cubic centimeters). The admixture containing the dissolved block copolymer was stirred for about 20 minutes at a pH of 6.88 and a temperature of about 22° centigrade. A Factor VIII containing precipitate was formed which was separated from the supernate by centrifuging the admixture at 5,000 gravities for about 20 minutes. The supernate was discarded.

FACTOR VIII REDISSOLVED

The resulting Factor VIII precipitate was redissolved in one milliliter of citrated saline having the composition described above and the resultant solution was further diluted for assay purposes to a total volume of 8 milliliters. In order to maintain the potency of the Factor VIII during the lyophilization 1 weight percent (grams per 100 cubic centimeters) of human albumin was added. This 8 milliliter volume of stabilized Factor VIII concentrate contained no clottable fibrinogen, as determined by conventional in vitro bioassay procedures.

YIELD

The crude fibrinogen containing Factor VIII concentrate starting material contained 1,250 units of Factor VIII, and the final concentrated fibrinogen free product contained 975 units of Factor VIII for a yield of 78 percent. A portion of the Factor VIII was lost in the bioassay procedures which were carried out at various points in the preparation of the fibrinogen free highly potent Factor VIII concentrate. Disregarding loses due to the withdrawal of samples for bioassay purposes, the yield is approximately 90 percent. A yield of this magnitude in a commercial scale operation results in the conservation of raw material which must be obtained from human donors and is in short supply. In a commercial scale operation the starting material would have a volume of at least 10 liters with a potency of approximately 4.7 units per milliliter of Factor VIII.

LYOPHILIZATON FOR STORAGE AND TRANSPORTATION

The salt concentration was adjusted to 0.15 molar sodium chloride and the product was lyophilized. Upon reconstitution the lyophilized product was found to have retained its potency and to be suitable for administration to hemophiliac patients. No trace of the thrombin mimetic enzyme remained in the product. The lyophilization procedure required about 36 hours. The balance of the procedure, exclusive of the lyophilization procedure, required about 32 hours. Except for the lyophilization step the procedure was carried out at room temperature.

EXAMPLE II

Repetition of Example I twice utilizing sodium chloride concentrations throughout of 0.25 and 0.05 molar sodium chloride, respectively, results in achieving satisfactory yields of Factor VIII.

Repetition of Example I utilizing the lower molecular weight block copolymer which is identified by the brand name "Pluronic F-38," and described hereinabove, produces satisfactory yields. In general, concentrations of the block copolymer are about 0.5 gram percent higher than for the Pluronic F-68, so that the initial fibrinogen precipitation step utilizes a concentration of 4 gram percent, and the Factor VIII precipitation steps utilize a concentration of about 12 gram percent.

Repetition of the lyophilization procedures of Example I results in the preparation of a lyophilized material, which when placed in a none milliliter capacity vial may be reconstituted with one milliliter of sterile water so as to produce an injectable Factor VIII concentrate material. The lyophilization procedure is repeated on successive samples having different Factor VIII potencies so that the reconstituted one milliliter solution will contain respectively 300, 1,000 and 2,500 units of Factor VIII (30, 100, and 250, respectively, units of Factor VIII per milligram of human albumin). Each of these is suitable for injection in an hemophiliac patient. Because of the absence of fibrinogen, there materials are suitable for intramuscular injection.

What is claimed is:
1. Process comprising:
    selecting an admixture containing clottable fibrinogen and Factor VIII;
    removing most of the clottable fibrinogen from said admixture to produce a clottable fibrinogen lean Factor VIII product;
    concentrating said product to produce a concentrate;
    admixing said concentrate with an amount of thrombin mimetic reagent sufficient to clot all of the clottable fibrinogen in said concentrate within approximately 24 hours without significantly impairing the potency of said Factor VIII, and allowing said clottable fibrinogen to form a clot;
    separating said clot and retaining a clottable fibrinogen free Factor VIII concentrate;
    admixing said retained clottable fibrinogen free Factor VIII concentrate with an amount of human albumin sufficient to stabilize said Factor VIII; and
    lyophilizing the resultant stabilized Factor VIII.
2. Process of claim 1 wherein approximately 90 percent of the clottable fibrinogen is removed from said admixture.
3. Process of claim 1 wherein said clottable fibrinogen lean Factor VIII product is concentrated to a Factor VIII potency of at least approximately 15 units.
4. Process of claim 1 wherein said process is carried out at a temperature of from about 10° to 35° centigrade.
5. Process of claim 1 wherein said process is carried out at a salt concentration of from about 0.05 to 0.25 molar sodium chloride.
6. Process of claim 1 wherein said process is carried out at a pH of from about 6.0 to 8.0.
7. Process of claim 1 wherein said resultant stabilized Factor VIII is lyophilized to produce a lyophilized product containing at least about 20 units of Factor VIII per milligram of human albumin.
8. A process of lyophilizing clottable fibrinogen free Factor VIII concentrate comprising:
    preparing an aqueous liquid admixture of said Factor VIII concentrate and at least about 0.5 percent on a weight per volume basis of human albumin; and
    lyophilizing said aqueous liquid admixture.
9. A lyophilized clottable fibrinogen free Factor VIII product comprising clottable fibrinogen free Factor VIII and human albumin and containing at least about 10 units of Factor VIII per milligram of albumin.
10. A lyophilized clottable fibrinogen free Factor VIII product comprising clottable fibrinogen free Factor VIII and human albumin and containing at least approximately 100 units of Factor VIII per milligram of albumin.

11. A lyophilized clottable fibrinogen free Factor VIII product comprising clottable fibrinogen free Factor VIII and human albumin and containing at least approximately 250 units of Factor VIII per milligram of albumin.

12. A lyophilized clottable fibrinogen free Factor VIII product comprising clottable fibrinogen free Factor VIII and at least about 0.5 percent on a weight per volume basis of human albumin.

13. Process comprising:
admixing a clottable fibrinogen lean Factor VIII concentrate containing less than approximately 0.2 milligrams of clottable fibrinogen per unit of Factor VIII with from about 0.5 to 3 units per 1000 milligrams of clottable fibrinogen of a thrombin mimetic reagent that does not significantly impair the potency of said Factor VIII, and allowing the clottable fibrinogen to form a clot in the resultant admixture separating said clot from said resultant admixture and recovering a clottable fibrinogen free Factor VIII concentrate;

admixing said clottable fibrinogen free Factor VIII concentrate with at least about 0.5 percent on a weight per volume basis of human albumin to stabilize said Factor VIII; and lyophilizing the resultant stabilized Factor VIII concentrate.

* * * * *